(12) United States Patent
Aulicino

(10) Patent No.: US 7,137,611 B2
(45) Date of Patent: Nov. 21, 2006

(54) PINCH CLAMP FOR FLEXIBLE TUBING

(75) Inventor: Robert Aulicino, Newton, NJ (US)

(73) Assignee: Ames Rubber Corporation, Hamburg, NJ (US)

( * ) Notice: Subject to any disclaimer, the term of this patent is extended or adjusted under 35 U.S.C. 154(b) by 0 days.

(21) Appl. No.: 10/959,273

(22) Filed: Oct. 5, 2004

(65) Prior Publication Data
US 2006/0071187 A1   Apr. 6, 2006

(51) Int. Cl.
F16K 7/00 (2006.01)

(52) U.S. Cl. .......................................................... 251/9

(58) Field of Classification Search ................ 251/4, 251/9, 10
See application file for complete search history.

(56) References Cited

U.S. PATENT DOCUMENTS

| | | | |
|---|---|---|---|
| 788,603 A * | 5/1905 | Rowell | ............... 251/9 |
| 2,212,571 A | 8/1940 | Martin | |
| 3,203,421 A * | 8/1965 | Bialick | ............... 128/885 |
| 3,544,138 A | 12/1970 | von Eiff | |
| D350,696 S | 9/1994 | Naslund | |
| D431,004 S | 9/2000 | Naslund | |
| D437,783 S | 2/2001 | Naslund | |
| 6,644,618 B1 * | 11/2003 | Balbo | ............... 251/10 |
| 6,708,377 B1 | 3/2004 | Maunder | |
| 2002/0109355 A1 * | 8/2002 | Elliott | ............... 285/410 |

* cited by examiner

Primary Examiner—J. Casimer Jacyna
(74) Attorney, Agent, or Firm—Greenberg Traurig LLP; Michael I. Wolfson; Sylvia Tan

(57) ABSTRACT

A pinch clamp to restrict flow in a flexible tube or hose is provided. The pinch clamp includes two elongated pinching members that are pivotally connected at one end with a threaded tightening member at the other end for selectively securing the pinching members in a closed position when the pinching members are pivoted toward each other. The inner cooperating faces of elongated pinching members have flat cooperating surfaces for engaging the flexible tube or hose.

16 Claims, 3 Drawing Sheets

PINCH CLAMP FOR FLEXIBLE TUBING

BACKGROUND OF THE INVENTION

The invention relates generally to clamps for pinching flexible tubing, and more particularly to a locking clamp suitable for pinching tubing and hoses used in the pharmaceutical and related industries.

A wide variety of clamps are available in the art. Many are used to connect flanged tubes. For example, U.S. Pat. No. 6,708,377 to Maunder discloses a tube clamp for sealing coupling two flanged tubes together. The clamp has two semi-circular coupling members with an inwardly facing tapered groove for drawing the two flanges into a sealing engagement. Similarly, U.S. Pat. No. 3,544,138 to Von Eiff discloses a coupling assembly for conduits. The coupling assembly has two annular members having a flat end face with grooves where a resilient gasket can be received to provide an effective seal to conduits when the annular members are clamped together. U.S. Pat. No. 2,212,571 to Martin discloses a union for connecting sections of pipe to form a fluid tight joint. The union has two adjacent tubular coupling members and a surrounding clamp ring to draw the coupling members together to form a fluid tight joint.

There is also a number of design patents related to clamps in the art used as bag clips. For example, U.S. Design Pat. No. D 350,696, No. D 431,004 and No. D 437,783 each disclose an ornamental design for a bag clip.

While these patents disclose a variety of clamps used to pinch hose, connect flanged tubes and ornamental designs for bag clips, there remains a need for a pinch clamp suitable for restricting fluid flow in a flexible tubing or hose for use in the pharmaceutical and food industries.

SUMMARY OF THE INVENTION

Generally speaking, in accordance with the invention, a pinch clamp for use in restricting fluid flow in a flexible tube or hose is provided. The pinch clamp includes two elongated pinching members that are pivotally connected at one end and have a threaded tightening member pivotally mounted at the opposite end for selectively securing the pinching members in a fixed closed position a selected distance apart when the pinching members are pivoted toward each other. The elongated pinching members of the clamp have cooperating projecting surfaces for engaging the flexible tube or hose. The elongated pinching members of the clamp are designed to support complete closure for the specific tubing and hose sizes. This is accomplished when the mating surfaces supporting the locking screw come together to indicate total closure. This also eliminates the need to torque the locking nut to ensure the clamp is in the closed position.

Accordingly, it is an object of the invention to provide an improved pinch clamp for restricting or metering fluid flow in a flexible hose or tubing.

It is another object of the invention to provide an improved pinch clamp for flexible hose or tubing that can be produced of inexpensive materials, such as plastics.

Yet another object of the invention is to provide a pinch clamp, for engaging a flexible hose having cooperating projecting surfaces with a selected distance therebetween for stopping the flow of fluid in the hose without damaging the tubing or hose.

Still other objects and advantages of the invention will in part be obvious and will in part be apparent from the specification.

The invention accordingly comprises a product possessing the features, properties, and the relation of components which will be exemplified in the product hereinafter described, and the scope of the invention will be indicated in the claims.

BRIEF DESCRIPTION OF THE DRAWINGS

For a fuller understanding of the invention, reference is had to the following description taken in connection with the accompanying drawing(s), in which.

DETAILED DESCRIPTION OF THE INVENTION

Figure 1:
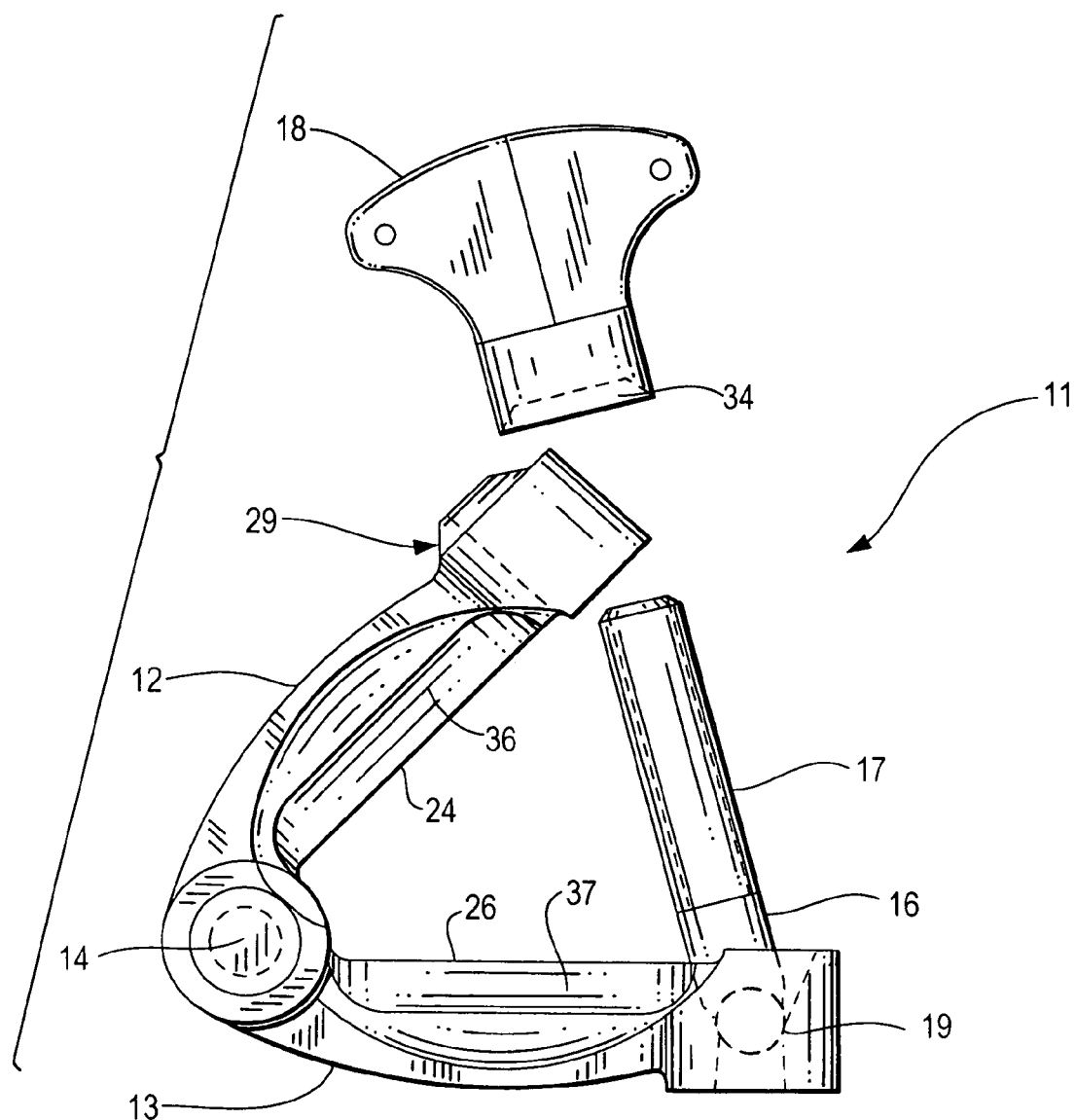
FIG. 1 is an elevational view of a pinch clamp constructed and arranged in accordance with the invention shown in an opened position.

An elevational view of a pinch clamp 11 constructed and arranged in accordance with the invention is shown in an opened position in FIG. 1. Clamp 11 includes an upper elongated pinching member 12 and a lower elongated pinching member 13. Elongated pinching member 12 and 13 each have an open end 12a and 13a, respectively, and an opposite closed end 12b and 13b, respectively. Members 12 and 13 are pivotally connected to their respective closed ends 12b and 13b at one end by a pin 14. Open ends 12a and 13a of elongated members 12 and 13 are selectively secured in a closed position by a threaded tightening member 16 pivotally mounted by a cross-head 19 secured to open end 13b of pinching member 13. Threaded tightening member 16 includes a screw 17 having a threaded end 17a with a wing nut 18 mounted thereon.

Figure 2:
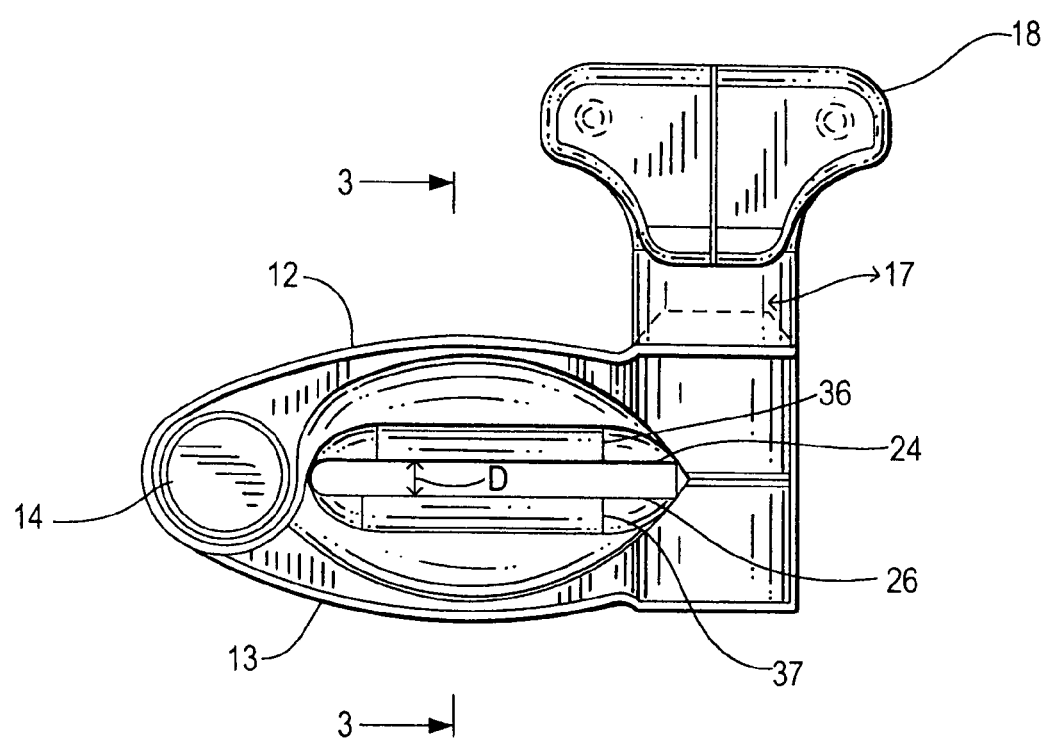
FIG. 2 is an elevational view of the pinch clamp of FIG. 1 in a closed position.

FIG. 2 is an elevational view of pinch clamp 11 in a closed position. Each elongated pinching member 12 and 13 has an inward facing elongated ridge or projections 22 and 23, respectively. Projection 22 on member 12 has extending inclined side surfaces 22a and 22b with a flat pinching surface 24. Projection 23 on member 13 has inclined side surfaces 23a and 23b and a flat pinching surface 26 cooperating with flat pinching surface 24. When flat face pinching surfaces 24 and 26 are a fixed distance D apart for pinching a flexible hose or tubing 31 placed between mating faces in the closed position, flow in tubing 31 is stopped. This is shown in FIG. 3 in the cross-sectional view of pinch clamp 11 taken along line 3—3 of FIG. 2.

Figure 3:
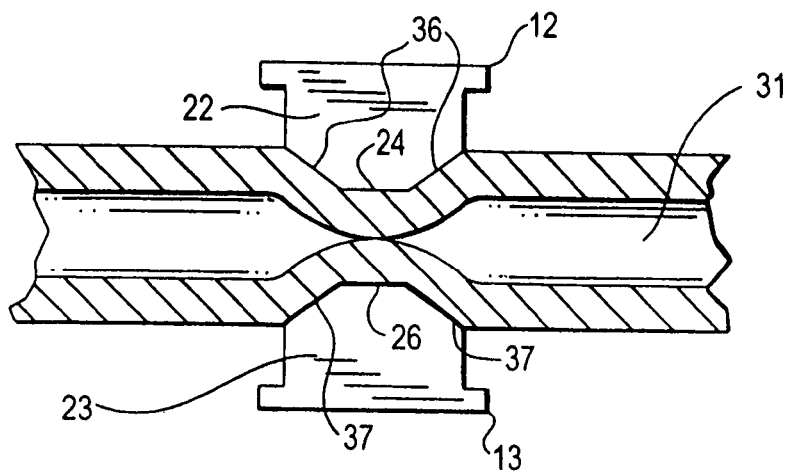
FIG. 3 is a cross-sectional front view of the pinch clamp of FIG. 2 engaging a piece of flexible tubing taken along line 3—3 of FIG. 2.

As shown in FIG. 3, flat pinching faces 24 and 26 of pinching members 12 and 13 is shown to have flat cooperating pinching surfaces 24 and 26 with inclined edges 36 and 37, engaging hose 31. This effectively restricts flow of a fluid in hose 31.

Figure 4:
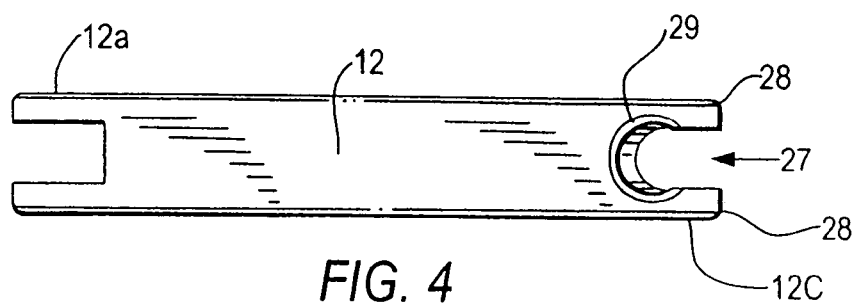
FIG. 4 is a top plan view of the upper elongated pinching member of the clamp of FIGS. 1 and 2.

FIG. 4 is a top plan view of upper elongated pinching member 12 showing a U-shaped opening 27 defined by two lugs 28. A frusto-conical formation 29 is formed at the U-shaped inner edge of opening 27. Wing nut 18 has a complementary conical recess 34 to capture conical formation 29 when clamp 11 is closed and wing nut 18 is tightened. These mating surfaces ensure complete closure.

Engagement of conical formation 29 in recess 31 restrains lugs 28 from separating under load as wing nut 18 is tightened. As wing nut 18 is tightened, mutual approach of the elongated pinching members is limited by mating surfaces 24 and 26 of pinching members 12 and 13. A side view of the frusto-conical formation 29 of the upper pinching member 12 and the complementary conical recess 34 of the wing nut 18 is shown in FIG. 1.

Figure 5:
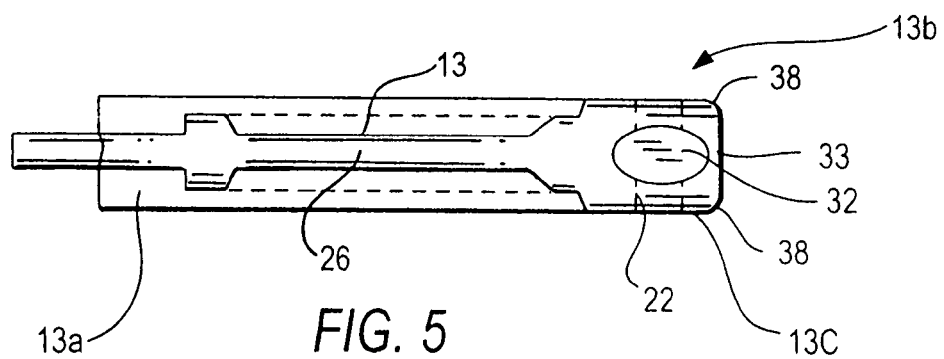
FIG. 5 is a top plan view of the lower elongated pinching member of the clamp of FIGS. 1 and 2.

FIG. 5 is a top plan view illustrating the details of lower member 13. Open end 13a includes a U-shaped opening 32 for receiving cross-head 19. Threaded tightening member 17 is engaged by U-shaped opening 32 defined by two lugs 38 and crossbar 33 in lower member 13. This allows threaded end 17 to rotate to an open position as shown in FIG. 1. Threaded end 17a is limited in its angular displacement in the recess by crossbar 33 that limits the movement of threaded end 17a and stabilizes lugs 38 against relative displacement under load when wing nut 18 is tightened.

The construction of clamp 11 as described provides a secure means to pinch the flow in a flexible hose or tubing. Over tightening is not possible due to mating surfaces 12c and 13c of pinching members 12 and 13 which indicates closure. It also provides a clamp that is reusable.

A clamp constructed and arranged in accordance with the invention can be fabricated from a wide variety of materials, such as a metallic material or plastic. Metallic materials include steel and stainless steel. Plastic materials include any rigid polymeric material such as polyethylene, polyvinyl chloride, polystyrene, polyamides, polyesters, fluoropolymers and high-performance thermoplastics, such as polysulphones. The particular material selected will be dictated by the end use. In the case of use in the pharmaceutical and food processing industries, polysulphones are preferred. The polysulphone material is preferred in these applications due to the fact that it may be sterilized for multiple cycles. In addition, it is a FDA-compliant material.

The clamps may be utilized with a wide variety of tubing and hose materials. These include silicone, ameprene, C-Flex, or polyvinyl chloride.

The hose or tubing suitable for use with clamp 11 may be unreinforced or reinforced. In the case of unreinforced tubing, it should generally have a wall thickness between 0.070 to 0.250 inch (17.8 to 63.5 mm) and 0.090 to 0.190 inch (22.9 to 48.3 mm) in thickness. In the case of reinforced braided hose, the wall thickness may vary from about 0.70 to 0.20 inch (17.8 to 50.8 mm); and preferably 0.090 to 0.180 inch (22.9 to 45.7 mm) in thickness. In the illustrated embodiment, the clamp jaw length is approximately 1.10 inches (2.79 cm) in length. The overall length of the clamp is about 3.0 inches (7.62 cm). Thus, a clamp of these dimensions is suitable for use with hoses to about 0.625 to 0.75 inch (1.59 to 1.9 cm) in diameter. The gap between clamping or pinching faces 24 and 26 is 0.14 inch (35.56 mm). Clamp 11 can be constructed with longer lengths; however, as clamp 11 is enlarged the load on pinching members 12 and 13 increases. Larger clamps having longer flat clamping surfaces would be used for larger diameter hoses.

Accordingly, a clamp constructed and arranged in accordance with the invention is sanitary as it provides a smooth contour which is readily cleanable. The clamp may be autoclave or gamma irradiated for sterilization. It is also resistant to most chemicals and can be completely disassembled without the use of tools.

The clamp is reusable due to the durability of the rigid polymeric materials, and may be continuously reused. In addition, it is light-weight, providing durability, high strength and compatibility with on-line applications. Its light-weight and heavy-duty properties make it suitable for a wide variety of working pressure within tubing and hoses.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

The invention may be embodied in other specific forms without departing from the spirit or essential attributes of the invention. Accordingly, reference should be made to the appended claims, rather than the foregoing specification, as indicating the scope of the invention.

What is claimed is:

1. A pinch clamp for restricting flow or metering in a flexible tube or hose comprising:
   a pair of substantially semi-circular pinching members having cooperating elongated pinching surfaces pivotally connected at one end; and
   a tightening assembly pivotally secured at the opposite end of one of the pinching members for selectively securing the pinching members in a closed position when the pinching members are pivoted toward each other;
   the elongated pinching surfaces on the pinching members have cooperating projections having inclined sides and substantially flat engaging surfaces for engaging the flexible tube or hose to restrict flow;
   the projections positioned on the pinching members to be directly opposed to each other and substantially parallel when the clamp is closed.

2. The pinch clamp of claim 1, wherein the tightening assembly includes a threaded screw mounted on one pinching member.

3. The pinch clamp of claim 1, wherein the pair of pinching members are pivotally connected with a pin.

4. The pinch clamp of claim 2, wherein the tightening assembly includes a conical formation on the second pinching member and a nut with recesses to engage the formation to restrain the lugs from separating under load as the nut is tightened.

5. The pinch clamp of claim 1, formed of a polysulphone.

6. A pinch clamp for metering or restricting flow in a flexible tube or hose comprising:
   a pair of substantially semi-circular pinching members having cooperating elongated pinching surfaces pivotally connected at one end, where the pinching members have cooperating projections for engaging the flexible tube or hose to restrict flow therein;
   each projection having inclined sides and substantially flat engaging surface;
   a pin for pivotally connecting one end of the pinching members; and
   a tightening assembly pivotally secured at the opposite end of the pinching members for selectively securing the pinching members in a closed position when the pinching members are pivoted toward each so that the flat engaging surfaces are substantially parallel to each other; and one of the pinching members having an opening with a crossbar for limiting angular displacement of the tightening assembly.

7. The pinch clamp of claim 6, wherein the tightening assembly includes a nut and screw.

8. The pinch clamp of claim 7, wherein the screw has a cross-head for engaging in an opening of one of the pinching members.

9. The pinch clamp of claim 8, wherein the opening is defined by two lugs with a recess in which the cross-head clips.

10. The pinch clamp of claim 9, wherein the nut engages with a conical formation on the recess to restrain the lugs from separating under load as the nut is tightened.

11. A pinch clamp for restricting flow in a flexible tube or hose comprising:
   a pair of substantially semi-circular pinching members having cooperating elongated pinching surfaces pivotally connected at one end, where the pinching members have cooperating projections for engaging the flexible tube or hose to restrict flow therein;
   each projection having inclined sides and a substantially flat engaging surface;
   a pin for pivotally connecting one end of the pinching members; and
   a screw and nut at the opposite end of the pinching members for detachably connecting the pinching members in a closed position when the pinching members are pivoted toward each and the flat engaging surfaces substantially parallel to each other; and
   one of the pinching members has an opening with a crossbar for limiting angular displacement of the screw.

12. The pinch clamp of claim 11, wherein the screw has a cross-head for engaging in an opening of one of the pinching members.

13. The pinch clamp of claim 12, wherein the opening is defined by two lugs with a recess in which the cross-head clips.

14. The pinch clamp of claim 11, wherein the nut engages with a conical formation on the recess to restrain the lugs from separating under load as the nut is tightened.

15. A clamp, comprising:
   a pair of substantially semi-circular pinching members hinged together at one end and connectable together at the other end by a screw and nut;
   the pinching members having mating faces with cooperating projections formed with inclined sides a flat pinching face to pinch a tube and an opening for receiving the screw;
   the flat pinching faces being substantially parallel when the clamp is closed;
   the screw having a cross-head for engaging in the opening of one of the pinching members; and
   the opening having a cross-bar distal of the pinching member for limiting angular displacement of the screw.

16. The pinch clamp of claim 15, wherein the opening in the member is defined by two lugs having a recess into which the cross-head clips.

* * * * *